(12) United States Patent
Rameshwar

(10) Patent No.: US 7,807,462 B2
(45) Date of Patent: Oct. 5, 2010

(54) METHOD FOR PRODUCING A FUNCTIONAL NEURON

(75) Inventor: Pranela Rameshwar, Maplewood, NJ (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 10 days.

(21) Appl. No.: 11/274,004

(22) Filed: Nov. 15, 2005

(65) Prior Publication Data

US 2006/0105457 A1    May 18, 2006

Related U.S. Application Data

(60) Provisional application No. 60/628,284, filed on Nov. 16, 2004.

(51) Int. Cl.
C12N 5/08 (2006.01)
C12N 5/00 (2006.01)

(52) U.S. Cl. .................................. 435/368; 435/325

(58) Field of Classification Search ............... 435/368, 435/325
See application file for complete search history.

(56) References Cited

U.S. PATENT DOCUMENTS

2003/0211603 A1* 11/2003 Earp et al. .................. 435/366

OTHER PUBLICATIONS

Hung, SC et al. Stem Cells 20:525-529, 2002.*
Kim, BJ et al. NeuroReport 13(9):1185-1188, 2002.*
Seigel, GM et al. Molecular Vision 9:159-163, Apr. 2003.*
Sanches-Ramos, J et al. Experimental Neurology 164:247-256, 2000.*
Chiu, FC et al. J Neurosci Res 38(6):abstract, 1994.*
Jochems, CEA. "Use, Trade, and Harvest of Livestock Sera", Utrecht Univeristy and Wagenin Agricultural Univeriuity, Thesis, 1997. Obtained online at http://www.vet.uu.nl/nca/userfiles/other/report_use_trade_and_harvest_of_livestock_sera_.pdf.*
Angelopoulou et al., "Cotransplantation of human mesenchymal stem cells enhances human myelopoiesis and megakaryocytopoiesis in NOD/SCID mice", Experimental Hematology 2003 31:413-420.
Bianco et al., "Bone Marrow Stromal Stem Cells: Nature, Biology, and Potential Applications", Stem Cells 2001 19:180-192.
Castro et al., "Failure of Bone Marrow Cells to Transdifferentiate into Neural Cells in Vivo", Science 2002 297:1299.
Cogle et al., "An Overview of Stem Cell Research and Regulatory Issues", Mayo Clin Proc 2003 78:993-1003.
Conti et al., "Cytokines and Fever", Frontiers in Bioscience 9 2004 1433-1449.
Deans et al., "Mesenchymal stem cells:Biology and potential clinical uses", Experimental Hematology 2000 28:875-884.
Dezawa et al., "Specific induction of neuronal cells from bone marrow stromal cells and application for autologous transplantation", J. Clin. Invest 2004 113(12):1701-1710.

Herzog et al., "Plasticity of marrow-derived stem cells", Blood 003 102(10):3483-3493.
Hescheler et al., "Indispensable tools:embryonic stem cells yield insights into the human heart", J. Clin. Invest. 2001, 108(3):363-364.
Hofstetter et al., "Marrow stromal cells form guiding strands in the injured spinal cord and promote recovery", Proc. Natl. Acad. Sci. USA 2002 99(4):2199-2204.
Ikehara S., "Allogenic Hematopoietic Stem Cell Transplantation for Autoimmune Disease", Bone Marrow Transplantation 2003 32:S73-S75.
Jiang et al., "Pluripotency of mesenchymal stem cells derived from adult marrow", Nature 2002 418:41-49.
Kehat et al., "Human embryonic stem cells can differentiate into myocytes with structural and functional properties of cardiomyocytes", J. Clin. Invest. 2001 108(3):407-414.
Koc et al., "Mesenchymal stem cells—Allogeneic mesenchymal stem cell infusion for treatment of metachromatic leukodystrophy (MLD) and Hurler syndrome (MPS-IH)", Bone Marrow Transplantation 2002 30:215-222.
Luyten, Frank P., "Mesenchymal stem cells in osteoarthritis", Current Opinion in Rheumatology 2004 16:599-603.
Ma et al., "Colocalization of CGRP with 5-HT $_{1B/1D}$ receptors and substance P In trigeminal ganglion neurons in rats", European Journal of Neuroscience 2001 13:2099-2104.
Meyer et al., "Neural differentiation of mouse embryonic stem cells in vitro and after transplantation into eyes of mutant mice with rapid retinal degeneration", Brain Research 2004 1014:131-144.
Montufar-Solis et al., "Using Cartilage to Repair Bone:An Alternative Approach in Tissue Engineering", Annals of Biomedical Engineering 2004 32(3):504-509.
Morrison et al., "The Biology of Hematopoietic Stem Cells", Annu. Rev. Cell Dev. Biol. 1995 11:35-71.
Muñoz-Elias et al., "Adult Bone Marrow Stromal Cells in the Embryonic Brain:Engraftment, Migration, Differentiation, and Long-Term Survival", J. Neurosci. 2004 24(19):4585-4595.
Nishimura et al., "Potential Use of Embryonic Stem Cells for the Treatment of Mouse Parkinsonian Models:Improved Behavior by Transplantation of In Vitro Differentiated Dopaminergic Neurons from Embryonic Stem Cells", Stem Cells 2003 21:171-180.
Orlic et al., "Mobilized bone marrow cells repair the infarcted heart, improving function and survival", Proc. Natl. Acad. Sci. USA 2001 98(18):10344-10349.

(Continued)

Primary Examiner—Thaian N Ton
Assistant Examiner—Marcia S Noble
(74) Attorney, Agent, or Firm—Licata & Tyrrell P.C.

(57) ABSTRACT

The present invention relates to the production of functional neurons from adult human mesenchymal stem cells using a retinoid. A retinoid, when used in the absence of a growth factor, transdifferentiates mesenchymal stem cells into functional neurons that exhibit synaptic transmission. Moreover, polarization of the functional neurons can be achieved using selected growth factors. Functional neurons produced in accordance with the method of the invention find use in the treatment or amelioration of diseases or conditions associated with neurodegeneration or nerve damage.

1 Claim, No Drawings

OTHER PUBLICATIONS

Orlic et al., "Bone marrow cells regenerate infarcted myocardium", Nature 2001 410:701-705.

Park et al., "Generation of dopaminergic neurons in vitro from human embryonic stem cells treated with neurotrophic factors", Neuroscience Letters 2004 359:99-103.

Petersen, Byron E., "Hepatic "Stem" Cells:Coming Full Circle", Blood Cells, Molecules, and Diseases 2001 27(3):590-600.

Potian et al., "Veto-Like Activity of Mesenchymal Stem Cells:Functional Discrimination Between Cellular Responses to Alloantigens and Recall Antigens", J. Immunol. 2003 171:3426-3434.

Prockop et al., "One strategy for cell and gene therapy:Harnessing the power of adult stem cells to repair tissues", Proc. Natl. Acad. Sci. USA 2003 100(1):11917-11923.

Proia et al., "Blood to brain to the rescue", J. Clin. Invest. 2004 113(8):1108-1110.

Qian et al., "Improving the expansion and neuronal differentiation of mesenchymal stem cells through culture surface modification", Biomaterials 2004 25:1331-1337.

Qian et al., "Cloning of Human Preprotachykinin-I Promoter and the Role of Cyclic Adenosine 5'-Monophosphate Response Elements in Its Expression by IL-1 and Stem Cell Factor[1,2]", J. Immunol 2001 166:2553-2561.

Rameshwar, Pranela, Molecule of the Month—Substance P:A Regulatory Neuropeptide for Hematopoiesis and Immune Functions:, Clin. Immunol. Immunopathol. 1997 85:129-133.

Sanchez-Ramos et al., "Neural Cells Derived From Adult Bone Marrow and Umbilical Cord Blood", J. Neurosci. Res. 2002 69:880-893.

Sapienza, Carmen, "Imprinted gene expression, transplantation medicine, and the "other" human embryonic stem cell", Proc. Natl. Acad. Sci. USA 2002 99(16):10243-10245.

Shi et al., "Myogenic fusion of human bone marrow stromal cells, but not hematopoietic cells", Blood 2004 104(1):290-294.

Takahashi et al., "Role of Eras in promoting tumour-like properties in mouse embryonic stem cells", Nature 2003 423:541-545.

Ye et al., "Presynaptic Glycine Receptors on GABAergic Terminals Facilitate Discharge of Dopaminergic Neurons in Ventral Tegmental Area", J. Neurosci. 2004 24:8961-8974.

* cited by examiner

SEQUENCE LISTING

```
<160> NUMBER OF SEQ ID NOS: 3

<210> SEQ ID NO 1
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 1
actgccggag ccctttga                                                   18

<210> SEQ ID NO 2
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 2
atggccagat ctctcaca                                                   18

<210> SEQ ID NO 3
<211> LENGTH: 18
<212> TYPE: DNA
<213> ORGANISM: Artificial Sequence
<220> FEATURE:
```

```
-continued

<223> OTHER INFORMATION: Synthetic oligonucleotide

<400> SEQUENCE: 3
ttatgaaagg agtgcaat                                                  18
```

METHOD FOR PRODUCING A FUNCTIONAL NEURON

INTRODUCTION

This application claims the benefit of priority from U.S. provisional patent application Ser. No. 60/628,284, filed Nov. 16, 2004, the content of which is incorporated herein by reference in its entirety.

This invention was made in the course of research sponsored by the National Institutes of Health (Grant Nos. CA-89868, AA11989, AT001182). The U.S. government may have certain rights in this invention.

BACKGROUND OF THE INVENTION

Research studies on adult and embryonic stem cells (ESCs) have undergone significant advances during the past few years. Experimental evidence shows that both stem cells could have future benefits in the area of regenerative medicine. Adult stem cells have been shown to have potential benefits for such diseases or conditions as diabetes mellitus, liver disease, cardiac dysfunction, Alzheimer's disease, Parkinson's disease, spinal cord injuries, bone defects, and genetic abnormalities (Herzog, et al. (2003) Blood 102:3483-3493; Petersen (2001) Blood Cell. Mol. Dis. 27:590-600; Ikehara (2003) Bone Marrow Transpl. 32:S73-S75; Nishimura, et al. Stem Cells 21:171-180; Hescheler & Fleischmann (2001) J. Clin. Invest. 108:363-364; Orlic, et al. (2001) Nature 410:701-705; Kehat, et al. (2001) J. Clin. Invest. 108:407-414). Furthermore, adult stem cells have been extensively studied for repair of orthopedic conditions, such as bone, cartilage, and tendon defects (Luyten (2004) Curr. Opin. Rheumatol. 16:599-603; Montufar-Solis, et al. (2004) Ann. Biomed. Eng. 32:504-509).

ESCs are considered the prototype stem cells due to their innate ability to differentiate into all possible cells, and are therefore invaluable sources for tissue repair (Hescheler & Fleischmann (2001) supra). Despite the remarkable potential of ESC in medicine, the obvious limit is the need for a safe match with respect to the Major Histocompatibility Complex Class II (Cogle, et al. (2003) Mayo Clin. Proc. 78:993-1003). ESCs could become functionally unstable when placed in an in vivo microenvironment and develop into tumors (Takahashi, et al. (2003) Nature 423:541-545). Another important consideration for ESCs is the stage of development, since these cells might be in transit to committed cells and would therefore express various developmental genes. This molecular change might not be evident since the ESC might not show phenotypic changes. Thus, it is conceivable that cells generated from ESCs could be dysfunctional if the originating stem cells are already committed to form cells of another tissue. Given these arguments, clinical application of ESCs would require robust examination of gene expressions prior to the generation of different cell types.

Clinical application of hematopoietic stem cells (HSCs) is controversial. Some reports show evidence of transdifferentiation by HSC (Orlic, et al. (2001) Proc. Natl. Acad. Sci. USA 98:10344-10349). Others report that transdifferentiation of HSC could be mistaken by cell fusion between HSC and cells of other tissues (Sapienza (2002) Proc. Natl. Acad. Sci. USA 99:10243-10245). An issue that is overlooked with respect to HSCs is the low efficiency that one could achieve in their expansion by current in vitro methods. Thus, to acquire sufficient HSCs for clinical use would require invasive procedures upon the donors. Another issue with HSC is that a population of HSC that is deemed stem cells by phenotypic analyses is generally heterogeneous, and could include cells that are committed towards a particular lineage (Shi, et al. (2004) Blood 104:290-294). Future application of HSC in repair medicine requires further research with the appropriate cell subset. Given an ideal situation where the candidate HSC is identified, there are ethical issues on the amount of bone marrow aspirates that should be taken from a donor.

Accordingly, alternative use of adult stem cells has been examined (Castro, et al. (2002) Science 1297:1299). Mesenchymal stem cells (MSC) show promise among the adult stem cells. MSCs are major adult bone marrow stem cells with multilineage potential (Morrison, et al. (1995) Annu. Rev. Cell Dev. Biol. 11:35-71; Deans & Moseley (2002) Exp. Hematol. 28:875-884). MSC could be used across allogeneic barriers due to their unique immune property (Potian, et al. (2003) J. Immunol. 171:3426-3434). This property of MSC is demonstrated by the ability to facilitate bone marrow transplantation (Koc, et al. (2002) Bone Marrow Transpl. 30:215-222; Rinder, et al. (2003) Exp. Hematol. 31:413-420; Prockop, et al. (2003) Proc. Natl. Acad. Sci. USA 100:11917-11923; Proia & Wu (2004) J. Clin. Invest. 113:1108-1110; Angelopoulou, et al. (2003) Exp. Hematol. 31:413-420). Furthermore, MSC are easily obtained from adult bone marrow, and can be expanded by simple in vitro procedures (Bianco, et al. (2001) Stem Cells 19:180-192). MSCs have been shown to transdifferentiate into cells of other germ layers (Bianco & Robey (2001) Nature 414:118-121; Munoz-Elias, et al. (2004) J. Neurosci. 24:4585-4595).

The generation of MSCs into neurons has been studied (Hofstetter, et al. (2002) Proc. Natl. Acad. Sci. USA 99:2199-2204; Qian & Saltzman (2004) Biomaterials 25:1331-7; Jiang, et al. (2002) Nature 418:41-49). However, for the most part, these studies characterized the transdifferentiation of MSC based on morphology, phenotypic changes and action potential (Hofstetter, et al. (2002) supra; Qian & Saltzman (2004) supra; Jiang, et al. (2002) supra; Dezawa, et al. (2004) J. Clin. Invest. 113;1701-1710). Synaptic transmission has not been reported for neurons derived from MSC. Cells similar to MSCs have been shown to survive in the brain (Bianco & Robey (2001) supra).

Needed in the art is a method for generating functional neurons from adult human MSC. The present invention meets this long-felt need.

SUMMARY OF THE INVENTION

The present invention is a method for producing a functional neuron. The method involves contacting isolated adult human mesenchymal stem cells with a solution comprising a retinoid in the absence of a growth factor, so that functional neurons are produced. In particular embodiments, the functional neurons are subsequently polarized by contacting the functional neuron with at least one selected growth factor. Isolated functional neurons and polarized, functional neurons are also provided.

DETAILED DESCRIPTION OF THE INVENTION

It has now been found that exposing isolated adult human MSC to a retinoid in the absence of an exogenous growth factor, transdifferentiates the MSC into functional neurons, as determined by phenotypic and electrophysiological analysis. Advantageously, the functional neurons produced by the method of the present invention are capable of synaptic transmission, as evident by immunofluorescence for synaptophysin, and can be used in neuronal repair.

By way of illustration, MSC were treated with all-trans-retinoic acid and examined microscopically at 400× magnification. The purpose was to observe morphological changes as the cells were exposed to a known differentiating agent. Compared to the symmetrical morphology of untreated MSC, MSC treated for 1 day with retinoic acid showed a transition to cells with asymmetrical morphology. This change progressed to day 4 when the retinoic acid-treated MSC showed neuron-like structures. By day 7, the treated cells demonstrated structures of cell bodies with long thin processes and growth cones indicative of functional neurons.

It was subsequently determined whether the retinoic acid-treated MSC express neuron-specific proteins. Cells were labeled for MAP2, which predominantly labels the cell bodies and dendrites; Neurofilament to stain for cell bodies and axons; and nestin for changes in morphology to neuronal cells. Synaptophysin was also analyzed as it is an indicator of synaptic regions. Labeling with anti-MAP2 and anti-synaptophysin were performed at different times following retinoic acid treatment. Untreated MSCs stained dim with MAP2, but negative for synaptophysin. In contrast, retinoic acid-treated cells stained bright for MAP2 at each time point, i.e., day 6, day 9 and day 12 retinoic acid treatment. Cells stained for 6-day retinoic acid treatment showed predominance of MAP2, and slight fluorescence for synaptophysin. At day 9, retinoic acid-treated cells showed brighter fluorescence for synaptophsin. This pattern of synaptophysin increased up to day 12 of treatment. Patterns were similar in ten different experiments, each with MSC from a different bone marrow donor.

All cells treated with retinoic acid were negative for glial fibrillary acidic protein (GFAP). The percentage of functional neurons developed by retinoic acid treatment were 80±10 (n=100) by immunostaining for neurofilament, MAP2 and nestin. However, when the retinoic acid-treated cells were analyzed by electrophysiology, one hundred percent showed action potential (n=25). Transfer of MSC from propagation media (DMEM) to DMEM/F12 did not increase the percentage of functional neuron formation, but enhanced the formation of nestin-positive cells by two to three days. The results show that MSC treated with retinoic acid co-express MAP2 and synaptophysin beginning at day 6 of retinoic acid-treatment.

To determine whether the retinoic acid-treated MSCs show functions consistent with native neurons, cellular electrophysiological properties were analyzed using a whole-cell patch clamp technique. Record was made of action potentials under current clamp condition. Cells fired spontaneously and regularly with a frequency of 20 $s^{-1}$. The amplitude, measured from the resting membrane potential of −50 mV was 63.4±17.4 mV. The half-width and rise time of the action potentials were 19.25±0.73 ms and 3.39±0.11 ms (n=768 events), respectively. To determine whether the retinoic acid-treated cells could communicate with each other, postsynaptic currents were measured under voltage clamp condition. The frequency, amplitude, half rise time and decay time of the postsynaptic currents of cells were 2.49 $s^{-1}$, 29.9±1.3 pA, 12.96±0.89 ms, and 36.5±1.0 ms (n=171 events), respectively. The frequency, amplitude, half rise time and decay time of the postsynaptic currents of the cells were 1.24 $s^{-1}$, 6.1±0.2 pA, 1.84±0.13 ms, and 31.3±1.3 ms (n=99 events), respectively. Kinetic analysis indicated that while the decay of the postsynaptic currents of functional neurons in culture for 6 days could be fitted by a single exponential function, the decay of the postsynaptic currents of the functional neurons in culture for 15 days required two exponentials.

Administration or implantation of cultured neurons in a damaged tissue, in vivo, is influenced by the microenvironment. Thus, to determine whether a functional neuron could be influenced to express a particular neurotransmitter, expression of the preprotachykinin-I gene (PPT-I), which encodes the neurotransmitter substance P (SP), was analyzed. Regulation of the PPT-I gene has been studied in the context of inflammatory mediators that are presumed to be at the site of neural injury. IL-1 was selected because of its role in neural function (Munoz-Elias, et al. (2004) *J. Neurosci.* 24:4585-4595), its ability to induce the production of SP (Qian, et al. (2001) *J. Immunol.* 166:2553-2561), and its signature as a proinflammatory mediator (Rameshwar (1997) *Clin. Immunol. Immunopathol.* 85:129-133). Furthermore the receptor for IL-1 has been reported in neurons (Coti, et al. (2004) *Frontier Biosci.* 9:1433-1449). MSC, treated with retinoic acid for 6 days, were stimulated with 10 ng/mL of IL-1α for 16 hours and the cells studied for SP production by immunofluorescence using anti-SP. Treated cells were also labeled for synaptovesicle 2 to determine if SP is stored in synaptic vesicle. The studies used MSC exposed to retinoic acid for 6 days because this time frame also showed functional synaptic activity. Retinoic acid-treated MSC were labeled with anti-SP and anti-synaptovesicle. The two labels were overlaid to gain insight as to the location of SP. Since the anti-SP was diluted in 1% human serum albumin (HAS) and the immunofluorescence used indirect immunofluorescence, secondary antibody specificity was studied in parallel labeling with 1% HSA in lieu of anti-SP.

Six experiments with a different donor were performed. The results showed bright fluorescence intensity for SP in cells stimulated with IL-1α. Fluorescence intensities were significantly reduced when the cells were costimulated with IL-1-retinoic acid. This indicates that the effects of IL-1α were specific. Cells labeled with 1% HSA showed minimal fluorescence, which was subsequently used as background fluorescence to compare other labeling studies. The results show IL-1α can induce the production of SP in functional neurons generated from retinoic acid-treated MSC.

Since dim fluorescence was observed for SP in studies with unstimulated MSC treated with retinoic acid, the gene from which SP is produced, PPT-I, may have been expressed with low level of translation. Thus, it was determined whether the PPT-I gene was expressed in retinoic acid-treated MSC by in situ hybridization with a cocktail of three oligomers. Studies with functional neurons from three different bone marrow donors showed bright fluorescence in the cell bodies of neurons. Functional neurons labeled with sense oligonucleotides showed no fluorescence. The results indicate that the PPT-I gene is expressed in untreated MSC differentiated with retinoic acid.

Retinoic acid is a general differentiation and transdifferentiation agent for the generation of neurons (Ma, et al. (2001) *Eur. J. Neurosci.* 13:2099-2104). Retinoic acid has been shown to induce the differentiation of cells during embryonic maturation into distinct organs, including the generation of neurons (Meyer, et al. (2004) *Brain Res.* 1024:131-144; Park, et al. (2004) *Neursci. Lett.* 359:99-103). The method disclosed herein showed higher efficiencies in the generation of functional neurons compared to other reports (Sanchez-Ramos (2002) *J. Neurosci. Res.* 69:880-893). Further, functional neurons generated in accordance with the instant method could be subsequently treated with a growth factor to induce expression of a specific neurotransmitter. Moreover, the spontaneous post-synaptic currents reveal the existence of the functional synapses in these cells. Because communication is a unique characteristic of neuronal cells, these functional synapses indicate that the instant MSC have this important ability. Significantly, some of the spontaneous post-synaptic currents recorded from functional neurons in culture for 6 days had a half rise time around 2 ms, which is close to the rise time for synapses in native neurons (neurons in mid-brain slice, 1.23±0.02 ms, n=1729 events). Thus, MSC of the present invention find application in repair of damaged or disease neurons of a variety of organs.

Accordingly, the present invention is a method for producing a functional neuron by contacting an adult human mesenchymal stem cell with a solution containing a retinoid, in the absence of a growth factor, to transdifferentiate the mesenchymal stem cell into a functional neuron. As used in the context of the present invention, a growth factor is intended to include a neurotrophin, such as brain-derived neurotrophic factor (BDNF), ciliary neurotrophic factor (CNTF), platelet-derived growth factor (PDGF), nerve growth factor (NGF), neurotrophin-3, neurotrophin-4, fibroblast growth factor (FGF), epidermal growth factor (EGF), and sonic hedgehog (Shh).

As will be appreciated by one of skill in the art, an adult human mesenchymal stem cell is an undifferentiated cell isolated from the bone marrow of an adult human. As exemplified herein, mesenchymal stem cells can be isolated from an adult in accordance with standard medical practices (e.g., via aspiration) and separated from non-mesenchymal stem cells using art-established methods (see, e.g., Potian, et al. (2003) supra). In particular embodiments, the mesenchymal stem cell is grown to confluency (i.e., expanded) in culture medium to provide a population of cells capable of transdifferentiation into functional neurons. In other embodiments, the mesenchymal stem cell has not been modified by a recombinant method.

The step of contacting the mesenchymal stem cells with a retinoid in the absence of a growth factor can carried out under a variety of conditions. For example, the mesenchymal stem cell can be placed on petri dishes, slides, coverslips, and the like, with the retinoid added to the culture medium. As will be appreciated by the skilled artisan, mesenchymal stem cells are maintained in culture medium (e.g., a minimum essential medium such as DMEM/F-12, DMEM, F-12, MEM or NEUROBASAL™) throughout the method to maintain viability. As such, while the culture medium is necessary to support cell viability and growth, transdifferentiation of the mesenchymal stem cell into a functional neuron results from the addition of a retinoid to the culture medium. Retinoids useful in accordance with the instant method include, but are not limited to, retinoic acid, retinyl acetate, retinol, all-trans-retinoic acid, 9-cis retinoic acid, 13-cis-retinoic acid, and the like. In particular embodiments, the retinoic acid is all-trans-retinoic acid. In accordance with the present invention, the retinoic acid is provided in solution (e.g., saline or water) to the cultured mesenchymal stem cell at a concentration sufficient to stimulate transdifferentiation into a functional neuron. A suitable concentration of retinoid to effect transdifferentiation is in the range of 100 nM to 100 µM. In certain embodiments, the retinoid is used at a concentration ranging from 1 µM to 75 µM. In particular embodiments, the concentration of retinoid is in the range of 20 µM to 50 µM.

As exemplified herein, incubating mesenchymal stem cells in the presence of a retinoid for at least about 6 days produces a functional neuron exhibiting synaptic activity. As used in the context of the present invention "about" is intended to mean±12 hours of the indicated time. In one embodiment, incubation with the retinoid is between about 6 days and about 12 days. In another embodiment, incubation with the retinoid is between about six days and about 9 days. In certain embodiments, incubation is not more than 15 days. In a particular embodiment, incubation with the retinoid is at least about 6 days.

The neuron of the present invention is said to be functional not only by its action potential, but by the ability to communicate with other neurons through synaptic transmission. The functionality of a neuron of the invention can be determined in accordance with one or more of the methods disclosed herein, e.g., based upon asymmetrical morphological changes; expression (e.g., mRNA or protein) of neuron-specific proteins such as MAP2, neurofilament, nestin and synaptophysin; and cellular electrophysiological properties such as action potential and postsynaptic currents. Moreover, purity of the functional neurons produced by the method of the present invention can be obtained, for instance, as a ratio of cell-specific marker expressing cells to a total number of cells with flow cytometry using an antibody or an antibody fragment for each cell-specific marker.

Subsequent to production the functional neurons of the present invention can be used in therapeutic applications, or alternatively, the functional neuron can be polarized. As used herein, a polarized functional neuron refers to a functional neuron which expresses one or more specific neurotransmitters. Polarization of a functional neuron is achieved by contacting the functional neuron with at least one selected growth factor. As will be appreciated by the skilled artisan, the amount or type of growth factor(s) is selected based upon the desired neurotransmitter(s) to be expressed by the functional neuron. As exemplified herein, IL-1α can be selected to induce expression of SP. Similarly, fibroblast growth factor, epidermal growth factor, and platelet-derived growth factor can be selected to induce neurotransmitters and associated proteins such as gamma-aminobutyric acid, tyrosine hydroxylase and serotonin.

Isolated functional neurons and polarized functional neurons of the present invention find application in the treatment or amelioration of a variety of diseases or conditions including, but not limited to, neurodegenerative diseases such as Parkinson's disease, Alzheimer's disease, Down's syndrome, prion disease (for instance, Creutzfeldt-Jakob disease, bovine spongiform encephalopathy and the like), polyglutamine disease (bulbar spinal amyotrophy, Huntington's disease, spinocerebellar dystonia and the like), and amyotrophic lateral sclerosis; cerebral ischemia; demyelination; head injury; spinal damage; cerebral infarct and the like.

For the treatment or amelioration of a disease or condition, functional neurons and polarized functional neurons of the present invention can be provided as a cell pharmaceutical composition composed of neurons, as the active ingredient, in admixture with a pharmacological acceptable carrier (e.g., saline buffer). In addition, the cell pharmaceutical composition can contain other agents to facilitate the viability, differentiation or polarization of the neuron. In addition, functional neurons and polarized functional neurons of the present invention can be used for the manufacture of a medicament for treating a neurodegenerative disease or a nervous damage.

Treatment or amelioration of a neurodegenerative disease or nervous damage can be achieved by introducing (e.g., via injection or the like) an effective amount of a functional neurons and polarized functional neurons of the present invention into a neurodegenerative site or a site with nerve damage so that at least one sign or symptom associated with the neurodegenerative disease or nervous damage is treated or ameliorated. While the microenvironment of transplanted functional neurons may provide the necessary growth factors to achieve polarization, it is contemplated that polarization can be carried out in vitro prior to injection or by the addition of one or more exogenous growth factors at, or just after, the time of injection of the neuron (i.e., in vivo). Whether applied in vitro or in vivo, the growth factor selected can be tailored for the particular disease or condition to be treated or ameliorated. For example, treatment of Huntington's disease can be achieved by injecting GABAergic functional neurons polarized with BNDF into the caudate nucleus, whereas treatment of Parkinson's disease can be achieved by introducing a dopaminergic functional neuron polarized with Shh into the corpus striatum or midbrain substantia nigra.

Alternatively, mesenchymal stem cells can be coinjected with a retinoid at a neurodegenerative site or a site with nerve damage so that functional neurons are produced in situ. As with in vitro production, the mesenchymal stem cells can be polarized by endogenous or exogenous growth factors to effectuate the treatment or amelioration of a disease or condition associated with neurodegeneration or nerve damage.

The invention is described in greater detail by the following non-limiting examples.

EXAMPLE 1

Materials

Reagents. DMEM with high glucose, DMEM/F12 and L-glutamine were purchased from Life Technologies (Gaithersburg, Md.). Defined fetal calf serum (FCS) was purchased from Hyclone (Logan, Utah). All-trans-retinoic acid (RA), phosphate-buffered saline (PBS, pH 7.4), human serum albumin (HSA) and FICOLL™ HYPAQUET™ were purchased from Sigma (St. Louis, Mo.). Stock solution of RA was prepared in DMSO to 20 mM. VECTASHIELD® was purchased from Vector Laboratories (Burlingame, Calif.).

Antibodies and Cytokines. Rabbit anti-MAP2, nestin monoclonal antibody, rabbit anti-neurofilament (68 kDa) and GFAP monoclonal antibody were purchased from Chemicon (Temecula, Calif.). Anti-synaptic vesicle 2 monoclonal antibody was obtained from NOVO CASTRA (Newcastle, UK). FITC streptavidin, synaptophysin monoclonal antibody and synaptovesicle Protein 2 monoclonal antibody were obtained from Vector Laboratories. FITC-goat anti-rabbit IgG and non-immune mouse IgG were purchased from Sigma. PE-goat anti-rat IgG was obtained from Santa Cruz Biotechnology Inc. (Santa Cruz, Calif.). The following antibodies were purchased from Becton and Dickinson (San Jose, Calif.): PE-rat anti-mouse κ, rat anti-SP monoclonal antibody, PE- and FITC-isotype control, PE-conjugated CD14 monoclonal antibody, FITC-conjugated CD45 monoclonal antibody and PE-CD44 monoclonal antibody. FITC-fibroblasts monoclonal antibody were purchased from Miltenyi Biotec (Auburn, Calif.). SH2 monoclonal antibody was prepared from the ascites of mice injected intra-peritoneally with hybridoma according to established methods (Potian, et al. (2003) supra). Recombinant human IL-1α (rhIL-1α) was provided by Hoffman LaRoche (Nutley, N.J.). IL-1 receptor antagonist was purchased from R&D Systems (Minneapolis, Minn.) and was stored at 2.5 mg/mL. Rabbit anti-SP was purchased from Biogenesis (Brentwood, N.H.).

EXAMPLE 2

Culture of MSC

MSCs were cultured from bone marrow aspirates as is described in the art (Potian, et al. (2003) supra). Unfractionated bone marrow aspirates (2 mL) were diluted in 12 mL of DMEM containing 10% FCS (D10 media) and transferred to tissue culture FALCON™ 3003 petri dishes. Plates were incubated and at day 3, mononuclear cells were isolated by FICOLLT™ HYPAQUET™ density gradient and replaced in the culture plates. Fifty percent media were replaced with fresh D10 media at weekly intervals until the adherent cells were ~80% confluent. After four cell passages, the adherent cells were asymmetric, $CD14^-$, $CD29^+$, $CD44^+$, $CD34^-$, $CD45^-$, $SH2^+$, and $fibroblast^-$ (Potian, et al. (2003) supra).

EXAMPLE 3

RA-Treated MSC

MSCs, ~80% confluence, were trypsinized and subcultured in 35 mm FALCON™ 3001 petri dishes, superfrost plus slides (Fisher Scientific, Springfield, N.J.), or on round coverslips. Slides were placed in 17×100 mm tissue culture dishes and coverslips were placed in 35 mm suspension tissue culture dishes. Superfrost slides and coverslips were seeded with 500 cells in D10 media. RA was added to culture media at 30 μM final concentration. After 3-4 days, media were replaced with fresh media containing RA. At different times following RA treatment, cells were studied by immunofluorescence, electrophysiology and in situ hybridization for β-PPT-I and by immunocytochemistry for the neurotransmitter SP.

EXAMPLE 4

Immunofluorescence for Neural-Specific Markers

RA-treated MSCs were washed with PBS (pH 7.4) and incubated for 1 hour at room temperature with the following antibodies: rabbit anti-MAP2 and/or synaptophysin monoclonal antibody at final concentrations of 1/500 and 1/200 respectively. In other labeling studies, cells were incubated with anti-GFAP, anti-neurofilament or anti-nestin, each at 1/500 final concentration. Antibodies were diluted in 0.05% TWEEN™/PBS (PBT) for membrane permeabilization. Primary antibodies were developed with secondary FITC-goat anti-rabbit IgG and PE-rat anti-mouse κ, both at final concentrations of 1/500. Secondary antibodies were incubated for 45 minutes at room temperature in the dark. After labeling, cells were fixed with 0.4% paraformaldehyde and then covered with VECTASHIELD®. Slides were immediately examined on a 3-color immunofluorescence microscope (NIKON® Instruments Inc., Melvelle, N.Y.).

EXAMPLE 5

Immunohistochemistry for SP

MSC on superfrost slides were treated with RA. At day 6, cells were washed three times with sera-free DMEM and 25 ng/mL rhIL-1α in a total volume of 500 μL. Control cells were incubated in parallel with vehicle (PBS with 1% HSA). After 24 hours, cells were washed with PBS, and then incubated in PBT containing rabbit anti-SP (1/3000 final dilution) and/or synaptic vesicle protein 2 monoclonal antibody. The latter determined whether SP was stored in synaptic vesicles. SP and anti-synaptic vesicle protein 2 were detected with anti-rabbit IgG FITC and anti-mouse IgG1 κ PE, respectively. After this, cells were fixed with 0.4% paraformaldehyde,

EXAMPLE 6

In Situ Hybridization for β-PPT-I

MSC were cultured as above on superfrost slides and then washed with 0.05% PBT. Cells were hybridized by incubation with 500 μL of hybridization buffer (Sigma, St. Louis, Mo.). After 2 hours, slides were incubated with 200 μL of hybridization buffer containing a cocktail (200 ng/mL) of denatured biotin-conjugated β-PPT-1-specific oligo probes based on GENBANK Accession No. U37529 (Table 1). Control slides were incubated with a mixture of similar oligos in the sense orientations. Slides were subsequently incubated overnight at 37° C. in a humid chamber. Slides were washed with SSC solution and hybrids detected by incubation for 1 hour at room temperature with FITC-streptavidin at 1/500 dilution. Slides were covered with PBS and immediately examined with an immunofluorescence microscope.

TABLE 1

| β-PPT-I | Spanning Region | Nucleotide Sequence | SEQ ID NO: |
|---|---|---|---|
| Exon 3 | +210/+227 | 5'-act gcc gga gcc ctt tga-3' | 1 |
| Exon 5 | +350/+367 | 5'-atg gcc aga tct ctc aca-3' | 2 |
| Exon 7 | +429/+446 | 5'-tta tga aag gag tgc aat-3' | 3 |

EXAMPLE 7

Electophysiological Recordings

Electrophysiological recordings were conducted as described in the art (Ye, et al. (2004) *J. Neurosci.* 24:8961-8974). In brief, whole-cell patch-clamp configuration was used to record electrical activity with an AXOPATCH™ 200B amplifier (Axon Instruments, Union City, Calif.), a Digidata 1320A A/D converter (Axon Instruments, Union City, Calif.) and PCLAMP™ 9 software (Axon Instruments) Data were filtered at 2 KHz and sampled at 10 KHz. The junction potential between the patch pipette and the bath solutions was nulled just before forming the giga-seal. The liquid junction potential between the bath and the electrode was 3.3 mV, as calculated from the generalized Henderson equation with the Axoscope junction potential calculator (Barry (1996) *Axobits* 18:3-4). Taking into account an initial series resistance of 15-25 MΩ, after the standard 80% compensation, there remained a 3-5 mV error for 1 nA of current. The cells were differentiated with RA in a 35 mm culture dish (FALCONT™ 3001). These dishes were filled with standard external solution containing 130 mM NaCl, 5 mM KCl, 2 mM $CaCl_2$, 1 mM $MgCl_2$, 10 mM Hepes, 10 mM glucose (320 mosmol; pH set to 7.4 with NaOH,). The patch electrodes had a resistance of 3-5 MΩ when filled with 121 mM·KCl, 4 mM $MgCl_2$, 11 mM EGTA, 1 mM $CaCl_2$, 10 mM HEPES, 2 mM Mg-ATP and 0.1 mM GTP wherein the pH was adjusted to 7.2 with 1N KOH, and the osmolarity to 280 mosmol with sucrose. All recordings were made in these solutions at an ambient temperature of 20-23° C. Postsynaptic currents and action potentials were counted and analyzed using the Mini-Analysis program (Synaptosoft, Fort Lee, N.J.). Spontaneous events were checked visually.

---

What is claimed is:

1. A method of producing a neuron consisting of contacting a culture medium consisting essentially of an isolated adult human mesenchymal stem cell with 1 µM to 75 µM of a retinoid, transdifferentiating said stem cell into a neuron, polarizing the neuron by contacting the neuron with at least one growth factor capable of inducing expression of a neurotransmitter by said neuron, and determining the functional capacity of said neuron to produce an action potential, so that a neuron is produced which expresses neuron-specific proteins and produces an action potential.

* * * * *